(12) United States Patent
Briskin

(10) Patent No.: US 6,287,263 B1
(45) Date of Patent: Sep. 11, 2001

(54) SYSTEM FOR PROCESSING BURSTED AMPLITUDE MODULATED SIGNALS USING AN IMPEDANCE SENSOR

(75) Inventor: Boris Briskin, Vadnais Heights, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 09/247,004

(22) Filed: Feb. 8, 1999

(51) Int. Cl.$^7$ .................................................. A61B 5/0295
(52) U.S. Cl. ............................. 600/526; 600/547; 607/28
(58) Field of Search .................................. 600/547, 506, 600/507, 526; 607/28

(56) References Cited

U.S. PATENT DOCUMENTS

| | | | |
|---|---|---|---|
| 4,596,251 | 6/1986 | Plicchi et al. | 128/419 |
| 4,686,987 | * 8/1987 | Salo et al. | 607/24 |
| 4,823,797 | * 4/1989 | Heinze et al. | 600/481 |
| 5,311,088 | 5/1994 | Nelson | 307/520 |
| 5,391,190 | * 2/1995 | Pederson et al. | 607/23 |
| 5,440,264 | 8/1995 | Sevenhans et al. | 327/553 |
| 5,578,064 | 11/1996 | Prutchi | 607/19 |
| 5,718,720 | * 2/1998 | Prutchi et al. | 607/28 |
| 5,722,997 | 3/1998 | Nedungadi et al. | 607/28 |
| 5,824,029 | 10/1998 | Weijand et al. | 607/122 |

* cited by examiner

*Primary Examiner*—Kennedy Schaetzle
(74) *Attorney, Agent, or Firm*—Schwegman, Lundberg, Woessner & Kluth, P.A.

(57) ABSTRACT

A low power processing system for processing bursted amplitude modulated signals performing impedance-related measurements across a load including injecting current pulses of constant amplitude across the load using at least a first electrode and a second electrode, the current pulses including bursts of a plurality of pulses at a pulse frequency at which the current pulses are repeated, the bursts transmitted at a burst frequency; detecting voltages across at least a third electrode and a fourth electrode; high pass filtering the voltages to produce filtered voltages; amplifying the filtered voltages to produce amplified voltage signals; bandpass filtering the amplified voltage signals with a bandpass filter with a center frequency equal to approximately the pulse frequency to generate first filtered signals; rectifying the first filtered signals to produce rectified signals; integrating the rectified signals to produce integrated signals; sampling-and-holding the integrated signals after each burst to capture an integrated pulse value for each burst, creating a plurality of discrete integrated pulse values; and bandpass filtering the plurality of discrete integrated pulse values using a filter including an upper cutoff frequency less than the burst frequency to produce the output related to the time-varying impedance of the load. In one application, the first electrode is positioned near to an apex of a right ventricle, the second electrode is outside of the right ventricle, the third electrode and fourth electrode are located within the right ventricle and wherein the output is related to the time-varying impedance of the right ventricle during systole and diastole.

27 Claims, 6 Drawing Sheets

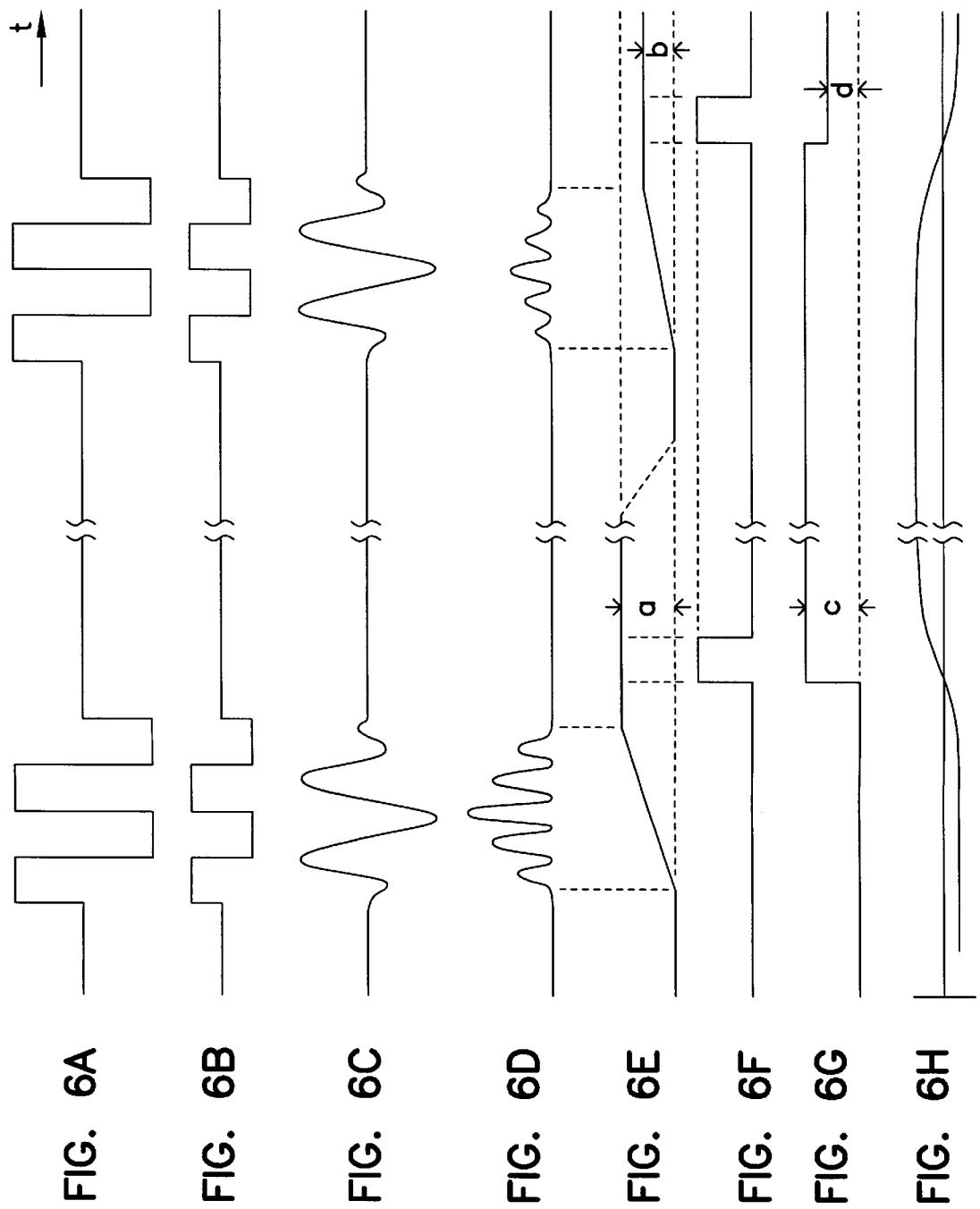

SYSTEM FOR PROCESSING BURSTED AMPLITUDE MODULATED SIGNALS USING AN IMPEDANCE SENSOR

FIELD OF THE INVENTION

This invention relates generally to a system for processing bursted amplitude modulated signals and in particular to method and apparatus for processing bursted amplitude modulated signals using an impedance sensor in biomedical applications.

BACKGROUND

The human body has electrical characteristics which can be measured for characterizing organ function and for the application of different therapies. For instance, the heart is a complex network of nerve and muscle tissue which operates in synchrony to pump blood throughout the body. Cardiac function may be monitored by sensing the electrical signals naturally conducted at certain places in the heart.

Sometimes it is convenient to apply signals to the body to determine the function of the organs of the body. For example, in ultrasound measurements a sound wave is transmitted into the body and the resulting reflections of the sound are used to image internal organs or a fetus.

Another way to apply signals is to use an implanted series of electrodes which apply a known current and measure the resulting voltage. The relationship between applied current and measured voltage is known as impedance. Thus, impedance is measured by injecting a known current using electrodes and monitoring the electrical voltage required to pass the known current between electrodes. The higher the magnitude of impedance, the higher the magnitude of voltage measured across the load for a known current magnitude.

If the electrodes are placed such that the impedance is measured across a right ventricular portion of the heart, then the impedance measured is a function of the stroke of the right ventricle. The stroke volume of the right ventricle provides a measure of the blood volume pumped by the heart into the lungs in one stroke.

The change in impedance is due to the conductive nature of blood and its changing volume in the left ventricle between contractions. The measured impedance will vary depending on the placement of the electrodes. For example, as shown in FIG. 1A and FIG. 1B, if a current is conducted between the housing of an implantable device 12 and a tip electrode 13 on the end of a catheter 14 with the tip electrode 13 positioned in the apex of the right ventricle 15, then the impedance observed between two electrodes, 16 and 17, located within the right ventricle (and before the tip electrode 13) will measure an increased impedance for a contracted ventricle (systole—FIG. 1B) as opposed to when the ventricle is not contracted (diastole—FIG. 1A). This is because in diastole, the ventricle is holding more blood and has more conductive volume to transfer current. In systole, the ventricle is contracted and has less blood, leaving less volume for conduction.

Impedance-based measurements of cardiac parameters such as stroke volume are known in the art. U.S. Pat. No. 4,674,518, issued to Salo, discloses an impedance catheter having plural pairs of spaced surface electrodes driven by a corresponding plurality of electrical signals comprising high frequency carrier signals. The carrier signals are modulated by the tidal flow of blood in and out of the ventricle. Raw signals are demodulated, converted to digital, then processed to obtain an extrapolated impedance value. When this value is divided into the product of blood resistivity times the square of the distance between the pairs of spaced electrodes, the result is a measure of blood volume held within the ventricle. These calculations may be made using spaced sensors placed within a catheter, as in the Salo '518 patent, or they may be derived from signals originating in electrodes disposed in the heart, as described in U.S. Pat. No. 4,686,987, issued to Salo and Pederson. The device of the '987 patent senses changes in impedance to determine either ventricular volume or stroke volume (volume of blood expelled from the ventricle during a single beat) to produce a rate control signal that can be injected into the timing circuit of another device, such as a cardiac pacer or drug infusion pump. In this manner, the rate of operation of the slaved device may be controlled. An example of application of this impedance sensing circuitry to a demand-type cardiac pacer is disclosed in U.S. Pat. No. 4,773,401, issued to Citak, et al.

However, many existing measurement systems in biomedical applications provide a continuous excitation of the tissue, and therefore current excitations must be carefully applied to avoid a current which would be unsafe or to avoid quickly depleting the batteries in an implantable device.

Thus, there is a need in the art for a low power signal processing system. The signal processing system should be flexible to provide low power processing of signals in biomedical applications, such as in the measurement of signals related to cardiac performance in implantable devices. In biomedical applications, the signal processing system should operate without requiring unsafe excitation signals and excessive power drain.

SUMMARY

Those skilled in the art, upon reading and understanding the present specification, will appreciate that the present signal processing system satisfies the aforementioned needs in the art and several other needs not expressly mentioned herein. A low power processing system for processing bursted amplitude modulated signals using an impedance sensor is provided. The processing system performs impedance-related measurements across a load including injecting current pulses of constant amplitude across the load using at least a first electrode and a second electrode, the current pulses including bursts of a plurality of pulses at a pulse frequency at which the current pulses are repeated, the bursts transmitted at a burst frequency; detecting voltages across at least a third electrode and a fourth electrode; high pass filtering the voltages to produce filtered voltages; amplifying the filtered voltages to produce amplified voltage signals; bandpass filtering the amplified voltage signals with a bandpass filter with a center frequency equal to approximately the pulse frequency to generate first filtered signals; rectifying the first filtered signals to produce rectified signals; integrating the rectified signals to produce integrated signals; sampling-and-holding the integrated signals after each burst to capture an integrated pulse value for each burst, creating a plurality of discrete integrated pulse values; and bandpass filtering the plurality of discrete integrated pulse values using a filter including an upper cutoff frequency less than the burst frequency to produce the output related to the time-varying impedance of the load.

In one application, the first electrode is positioned near to an apex of a right ventricle, the second electrode is outside of the right ventricle, the third electrode and fourth electrode are located within the right ventricle and wherein the output is related to the time-varying impedance of the right ventricle during systole and diastole.

In one embodiment, the output signal is analog-to-digital converted. The system may be used for estimating stroke volume using the output and/or estimating hemodynamic maximum sensor rate using the output. The system may be used for controlling pacing as a function of the output. Various electrode configurations and pulse parameters may be used. Low power embodiments are provided.

In one embodiment, the signal processing system comprises an excitation source coupled to at least a first electrode and a second electrode, the excitation source producing current pulses of constant current flowing between the first electrode and the second electrode, the pulses sent in bursts at a burst frequency and having a pulse frequency at which the pulses are repeated; a first high pass filter filtering voltage signals received by at least a third electrode and a fourth electrode to produce filtered voltage signals; an amplifier amplifying the filtered voltage signals; a first bandpass filter coupled to the amplifier and having a center frequency of approximately the pulse frequency; a rectifier coupled to the first bandpass filter and rectifying the filtered and amplified voltage signals to produce rectified signals; an integrator coupled to the rectifier and integrating the rectified signals to produce integrated signals; a sample-and-hold coupled to the integrator and sampling-and-holding the integrated signals to produce a plurality of samples; and a second bandpass filter coupled to the integrator and including an upper band cutoff frequency which is less than the burst frequency, the second bandpass filter filtering the plurality of samples to produce an output signal related to a time-varying impedance of a load.

In one embodiment, the apparatus includes the first electrode positioned near an apex of a right ventricle, the second electrode is outside of the right ventricle, the third electrode and fourth electrode are located within the right ventricle and wherein the output is related to the time-varying impedance of the right ventricle during systole and diastole. Other embodiments are provided and applications include estimation of stroke volume, minute ventilation and/or hemodynamic maximum sensor rate. Several embodiments are described in detail, however, one skilled in the art upon reading and understanding the specification will appreciate that other embodiments exist and that the present description is not intended in a limiting or exclusive sense.

This summary is intended to be a general overview of the present system and is not intended in a limiting or exclusive sense. The invention described in the detailed description has a scope provided by the attached claims and their equivalents.

BRIEF DESCRIPTION OF THE DRAWINGS

FIG. 6A is a trace of bursts of constant current, biphasic, pulses according to one embodiment of the present system.

FIG. 6B is a trace of voltage signals produced by the current pulses of FIG. 6A according to one embodiment of the present system.

FIG. 6C is a trace of filtered voltage signals of FIG. 6B, according to one embodiment of the present system.

FIG. 6D is a trace of rectified signals from FIG. 6C, according to one embodiment of the present system.

FIG. 6E is a trace of integrated signals from FIG. 6D, according to one embodiment of the present system.

FIG. 6F is a trace of the sample-and-hold signal, according to one embodiment of the present system.

FIG. 6G is a trace of discrete sampled-and-held signals from FIG. 6E using the sample-and-hold signal of FIG. 6F, according to one embodiment of the present system.

FIG. 6H is a trace of filtered signals from FIG. 6G, according to one embodiment of the present system.

DETAILED DESCRIPTION

This detailed description provides a number of different embodiments of the present method and apparatus. The embodiments provided herein are not intended in an exclusive or limited sense, and variations may exist in organization, dimension, hardware, software, mechanical design and configuration, and chemical aspects without departing from the claimed invention, the scope of which is provided by the attached claims and equivalents thereof.

The present signal processing system is demonstrated in the following detailed description in several embodiments. Some of the embodiments are demonstrated in applications involving implantable devices, such as pacemakers and cardioverter-defibrillators, however, it is understood that the present signal processing system may be used in any implantable device and may also be used by devices which are not implanted. Furthermore, the concepts provided herein are not limited to sensing in the right ventricle and different electrode configurations may be used without departing from the present system.

The following documents are all hereby incorporated by reference in their entirety: U.S. Pat. No. 4,674,518, issued to Salo, U.S. Pat. No. 4,686,987, issued to Salo and Pederson, U.S. Pat. No. 4,773,401 issued to Citak et al., U.S. Pat. No. 5,036,849, issued to Hauck et al., U.S. Pat. No. 5,156,147 issued to Warren et al., U.S. Pat. No. 5,235,976, issued to Spinelli, U.S. Pat. No. 5,391,190 to Pederson et al., and U.S. Pat. No. 5,792,195, issued to Carlson et al. These documents relate to a variety of systems and applications, including, but not limited to, stroke volume, minute ventilation, and maximum hemodynamic sensor rate ("HMSR") systems. However, any process or apparatus which may benefit from the present system may incorporate the present system and apply the teachings provided herein. Minor changes in filtering, order of processes, and signal conditioning do not necessarily depart from the present system, and the scope of the invention is determined by the attached claims and their equivalents.

Figure 1A:
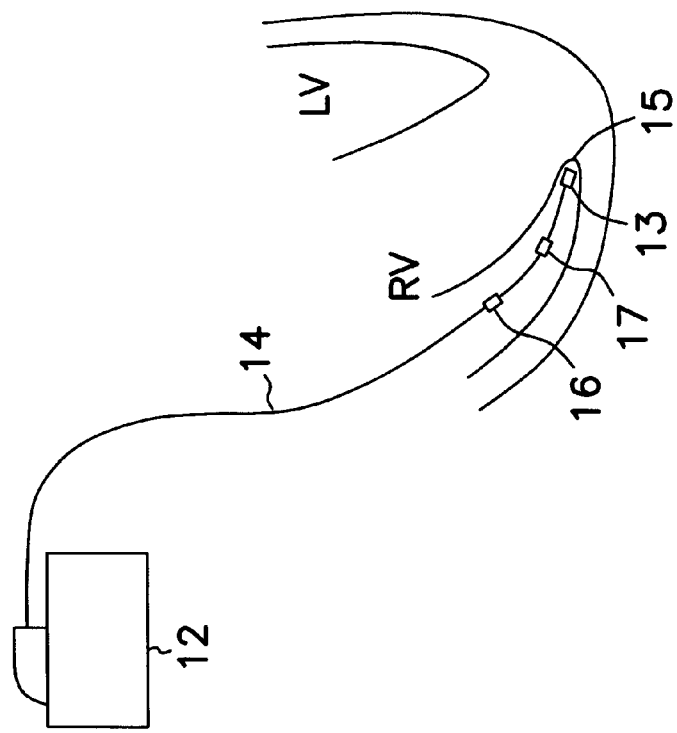
FIG. 1A is an example of an impedance measurement of a right ventricle of a heart in diastole.
Figure 1B:
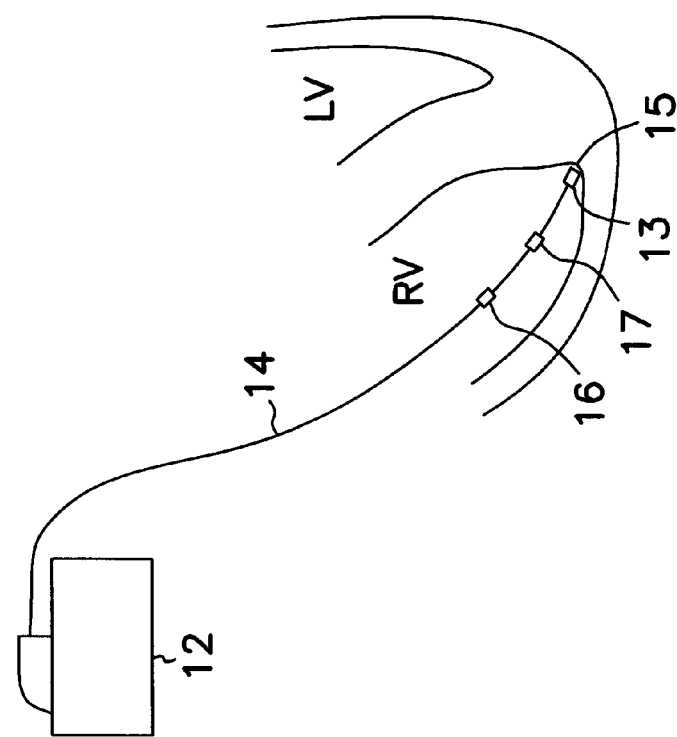
FIG. 1B is an example of an impedance measurement of a right ventricle of a heart in systole.

FIG. 1A is an example of an impedance measurement of a right ventricle of a heart in diastole. FIG. 1B is an example of an impedance measurement of a right ventricle of a heart in systole. If a current is conducted between the housing of an implantable device 12 and a tip electrode 13 on the end of a catheter 14 with the tip electrode 13 positioned in the apex of the right ventricle 15, then the impedance observed between two electrodes, 16 and 17, located within the right ventricle (and before the tip electrode 13) will measure an increased impedance for a contracted ventricle (systole—FIG. 1B) as opposed to when the ventricle is not contracted (diastole—FIG. 1A). This is because in diastole, the ventricle is holding more blood and has more conductive volume to transfer current. In systole, the ventricle is contracted and has less blood, leaving less volume for conduction.

Figure 2:
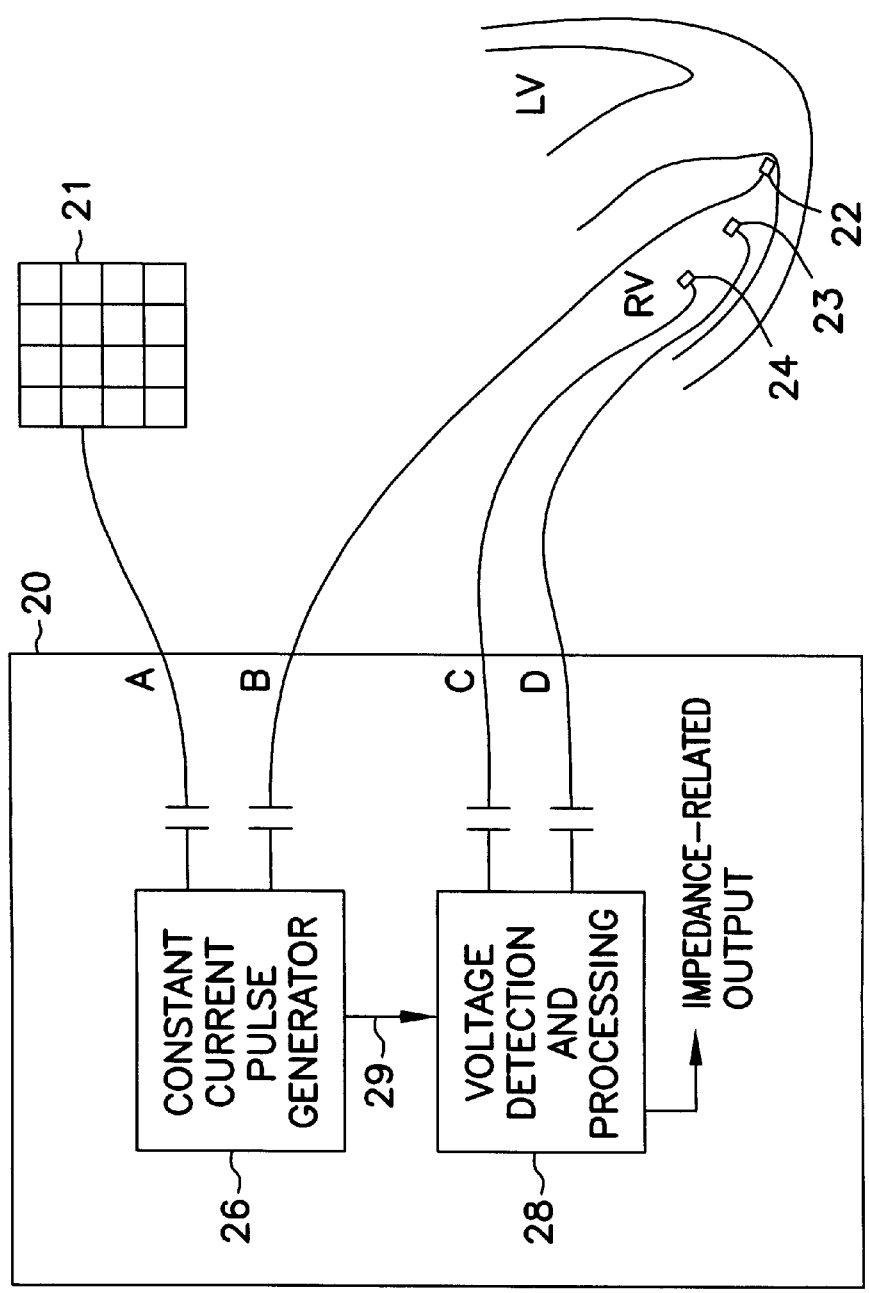
FIG. 2 is a block diagram showing a signal processing system according to one embodiment of the present system.

FIG. 2 is a block diagram showing a signal processing system according to one embodiment of the present system. Device 20 may be a pacemaker, cardioverter-defibrillator, or any other implantable device. Device 20 may also be located outside of the body. Electrodes 21 and 22 are located in the body in one embodiment. In one application electrode 21 may be an electrode external to the heart, including, but not limited to, a mesh, a catheter electrode, a patch electrode, or a conductive portion of the housing of an implantable device. If device 20 is an implantable device, then electrode 21 may be the conductive walls of the hermetically sealed device 20.

In one embodiment, electrode 22 is located near the apex of the right ventricle. Electrode 22 can be any type electrode, including, but not limited to, a tip electrode of a catheter electrode assembly.

In one embodiment, electrodes 21 and 22 are capacitively coupled to a constant current pulse generator 26. In one embodiment, the pulse generator 26 produces a number of different constant current waveforms. In one embodiment pulse generator 26 produces bursts of current pulses as shown in FIG. 5B. In this embodiment, these pulses are biphasic and are sent two at a time with a pulse frequency of 16 Khz and a burst frequency of 73 Hz. The pulses are constant current, which means that their 60 microamp peak-to-peak current value is regulated within 50 percent. In one embodiment, any current source design may be used to produce the constant current waveforms. Ideal constant current supplies have an infinite output impedance. In one embodiment the constant current source has a very large output impedance compared to the impedance load between the electrodes. In one embodiment the constant current source has an output which is greater than or equal to approximately 200 kiloohms. In embodiments where the electrodes are used to measure current across the cardiac area an output impedance of approximately 200 kiloohms was demonstrated to be adequate.

The waveform shown in FIG. 5B is useful for measurements of right ventricular function, since the burst frequency is greater than twice the right ventricular frequency range of interest, as required by the Nyquist theorem. For example, the right ventricular frequency of interest lies between approximately 0.1 Hz and 25 Hz. Any burst frequency exceeding approximately twice the upper limit satisfies the Nyquist theorem. In this example, a burst frequency exceeding approximately 50 Hz is adequate. Additionally, the pulse frequency is much greater than the Nyquist frequency, providing smaller pulses for low energy consumption. Other waveforms may be generated by pulse generator 26 without departing from the present system.

In one embodiment, electrodes 23 and 24 are capacitively coupled to voltage detection and processing electronics 28. Processing electronics 28 produces an output related to the relative impedances of the tissue measured. The processing of signals received by electrodes 23 and 24 is based on the constant current pulses generated by pulse generator 26. In one embodiment, signal 29 is used to coordinate sensing events between pulse generator 26 and processing electronics 28. In embodiments involving active pacing or defibrillation of heart tissue, the signal 29 is used to inhibit sensing by processing electronics 28. In one embodiment, signal 29 is produced by a pacemaker, cardioverter-defibrillator, or other stimulator operating as part of or in conjunction with device 20. In one embodiment, processing electronics 28 are blanked during excitation of the cardiac tissue. In one embodiment involving pacing, the device 20 is used in an HMSR application to pace using the relative impedance of cardiac tissue to determine a maximal pacing rate for optimal hemodynamic function. In one embodiment, the device 20 is used in a minute ventilation measurement application.

Electrodes 23 and 24 may be any type of electrodes, including, but not limited to, catheter electrodes mounted on a common catheter with electrode 22 being a tip electrode. Thus, the constant current pulses from pulse generator 26 are transmitted between electrodes 21 and 22, which creates a voltage gradient across electrodes 23 and 24 which is related to the impedance of the electrical pathways between electrodes 21 and 22. As shown before, during diastole the impedance is less due to the larger conduction volume of the blood filling the ventricle than which is present in systole.

Figure 3:
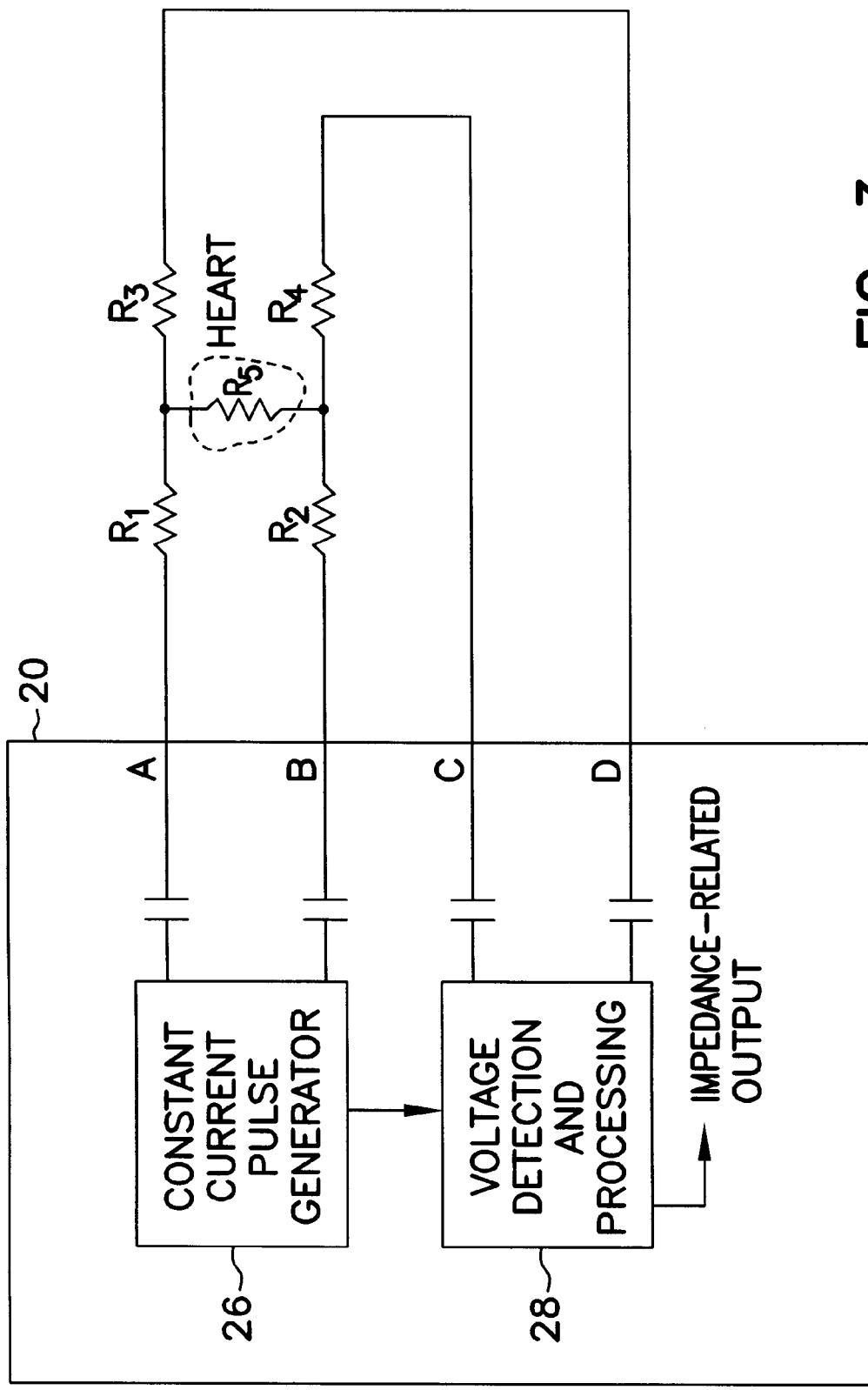
FIG. 3 is the block diagram of FIG. 2 where the heart and electrodes are modeled as impedances.

FIG. 3 relates to the block diagram of FIG. 2, except that the heart and electrodes are modeled as impedances. Impedances R1, R2, R3, and R4 are the impedances of the electrodes. Impedance R5 is the time-varying impedance of the heart's right ventricle.

Figure 4:
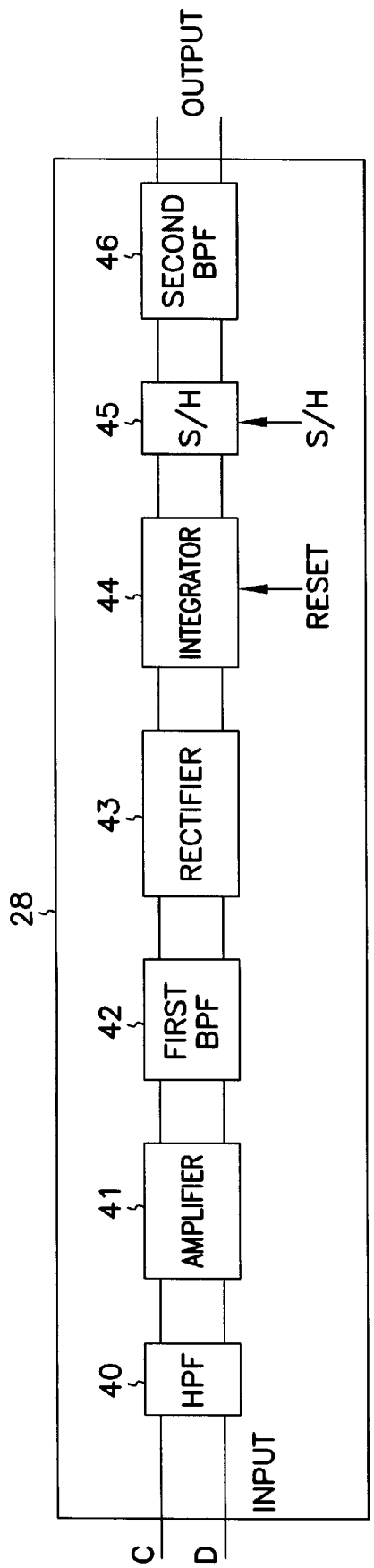
FIG. 4 is a block diagram of a signal processing system according to one embodiment of the present system.

FIG. 4 is a block diagram of voltage detection and processing electronics 28 according to one embodiment of the present system. The operation of processing electronics 28 in this embodiment is demonstrated by referring to FIG. 6 for the signal traces at the output of each stage.

For instance, pulse generator 26 (not shown in FIG. 4) provides the constant current pulses shown in FIG. 6A. The resulting voltage signals are received by electrodes 23 and 24 and sent to inputs C and D of processing electronics 28 and to high pass filter 40. The high pass filter 40 has a low frequency cutoff of approximately 1000 Hz in one embodiment. The high pass filter 40 has a cutoff frequency above the spectral range of the R-waves produced by the heart in a cardiac application. In the embodiment with the cutoff of approximately 1000 Hz, the R-wave components are blocked by low pass filter 40, but the 16 Khz pulses are passed. Amplifier 41 amplifies voltage signals from high pass filter 40. The amplified voltage signals are then bandpass filtered by first bandpass filter 42, as shown in FIG. 6C. The first bandpass filter 42 has a center frequency approximately equal to the carrier frequency of the constant current waveform, such as the pulse frequency in one embodiment of the present system. Such a filter removes spectral signals outside of the bandpass which are naturally generated as part of the square wave excitation signal and extracts substantially the fundamental frequency signal components, as is known from Fourier analysis of a square wave. The first bandpass filter selects a fundamental harmonic which is substantially sinusoidal and which may be processed by electronics tuned to the fundamental harmonic. In this way, the fundamental harmonic is the frequency of interest as it presents the best measure of signal-to-noise ratio. The Q of the filter is adjusted to optimize this signal-to-noise ratio of the substantially fundamental harmonic components of the received signal. In one embodiment, the first bandpass filter has a center frequency of 16 Khz and a Q of 3. In one embodiment, depending on the Q of the bandpass filter 42, the number of peaks of the sine wave shown in FIG. 6C may exceed the number of pulses per burst as shown in FIG. 6B.

Other embodiments provide different filter characteristics without departing from the present system. The first bandpass filter 42 is narrow enough to remove out of band extraneous noise which may have been amplified by amplifier 41.

The resulting first filtered signals are rectified by rectifier 43, as shown in FIG. 4, and the resulting signal traces are shown in FIG. 6D. The rectified signals are then integrated to produce a discrete integrated value for each burst of pulses. Integrator 44 is shown coupled to sample-and-hold 45 in FIG. 4. Integrator 44 is any type of known integrator or its equivalent. In one embodiment the integrated value is reset to zero after the sample-and-hold 45 acquires the signal. This relationship is shown in greater detail in FIG. 6E and FIG. 6F. After the integration of a burst of pulses is complete, sample-and-hold 45 is fired as shown in FIG. 6F to sample-and-hold the current value of the signal shown in FIG. 6E. The resulting sampled-and-held signal is shown in FIG. 6G. This signal is passed through the second bandpass filter 46 to produce a smoothed impedance-related signal, as shown in FIG. 6H. The bandpass filter output shown in FIG. 6H has the DC component removed, such as is provided by an embodiment incorporating a switched capacitor filter. The second bandpass filter has a bandpass in the region of frequency interest, which according to the Nyquist theorem must be less than half the burst frequency. This limits the amount of high frequency noise produced by the system and reduces the burst frequency artifacts in the resulting output signal.

If a first burst of pulses has greater average voltage than a second burst of pulses, then the integrated magnitude of the rectified pulses is greater for the first burst of pulses than for the second. In FIG. 6D the first burst of pulses on the left is exaggerated to show that it is higher in voltage than in the second burst of pulses on the right. The drawings are not to scale, and were exaggerated to demonstrate a point. Therefore, the integrated magnitude "a" from the first burst of pulses, shown in FIG. 6E, is greater than the integrated magnitude "b" from the second burst of pulses. The sample-and-hold pulses in FIG. 6F then capture different values in the sampled-and-held trace of FIG. 6G. Therefore, the magnitude "c" is greater than magnitude "d" indicating a higher average voltage in the first burst of pulses than in the second burst of pulses. This difference in voltage is related to a change in impedance of the load, since the injected current is substantially constant.

In one embodiment, the sample-and-hold 45 is triggered with a slight time delay so that any phase delay from the first bandpass filter 42 is accounted for and a premature sampling of the integrated value is avoided. In such embodiments, one sequence of events includes generation of a burst of several high frequency pulses which are integrated as described, followed by a sample-and-hold at a predetermined time delay to account for phase delay in the band pass filter 42, followed by a reset of the integrator.

In one embodiment, second bandpass filter is a switched capacitor filter having a lower cutoff frequency of 0.1 Hz and an upper cutoff frequency of 30 Hz. In the embodiment where signals are measured in the cardiac tissue, the resulting trace in FIG. 6H is related to the systolic and diastolic cycles, and may be used to calculate various cardiac performance parameters or to control the device 20.

In one embodiment, all of the connections between the various stages are fully differential for enhanced noise immunity of the circuit.

In one embodiment, the output signal is fed to an analog-to-digital convertor for further digital domain processing of the output signal. In one embodiment, the analog-to-digital convertor is a 12-bit design.

The present integrating system produces an output which is directed related to the energy of the rectified signal. This system also has considerable noise immunity and a relatively straightforward system for sampling-and-holding the integrated signal. Thus the need for complicated timing of the integrated signal is eliminated.

The output signal can be related to impedance due to the constant current nature injection of the excitation source. In one embodiment, the signal is a relative signal and not absolute due to the processing involved in converting a voltage signal into a rectified signal and integrated signal and sampled and held in band-pass filter. Different electrode placements may result in different output signals.

One benefit of the present system is that the carrier frequency of the modulated constant current signal (the pulse frequency in one example) is set at a frequency which is high compared to intra corporeal electrical noise in one embodiment. The large separation of frequency allows the processing electronics 28 to easily separate the impedance signal from electrical noise. For example, a pulse frequency of approximately 16 Khz is much greater than that of intra corporeal noise, such as the 0.1 to 100 Hz for intra cardiac ECM. Such a design provides good isolation between the impedance signal and any R-waves. The design also provides high impedance signal bandwidth for applications such as HMSR.

Another advantage of the new system is that the current level is minimized so as to reduce or completely eliminate impact to a surface ECG electrogram. In low constant current designs the need to perform cardiac sense amplifier blanking is reduced or completely eliminated. A micropower embodiment is provided by incorporating the teachings of the present system.

Figure 5A:
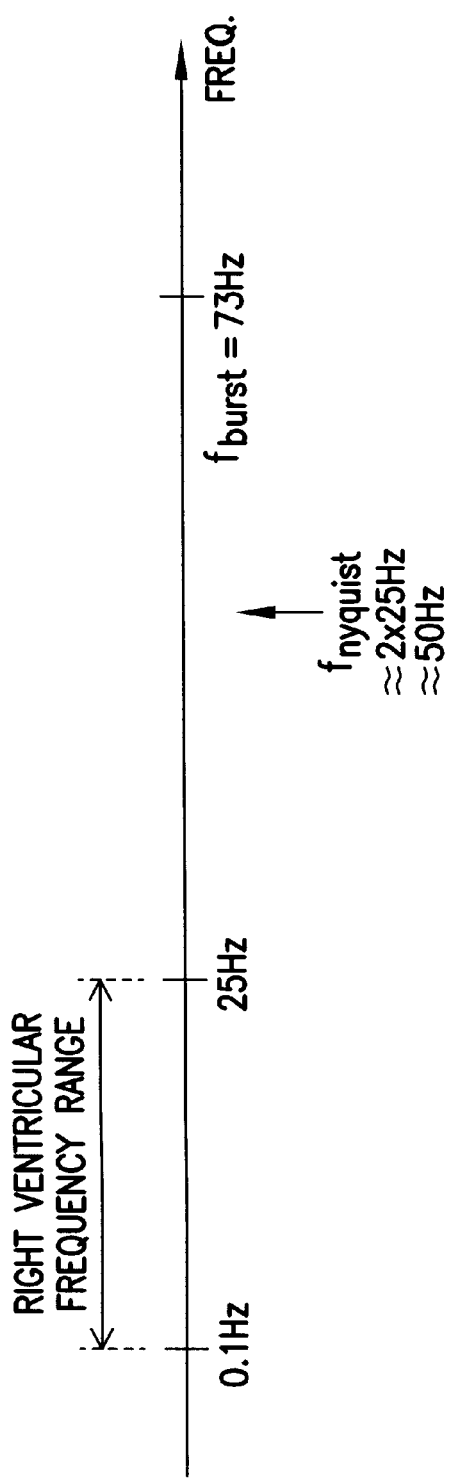
FIG. 5A is a frequency chart showing sampling frequency, Nyquist frequency, and the frequency range of interest for the right ventricular function, according to one embodiment of the present system.
Figure 5B:
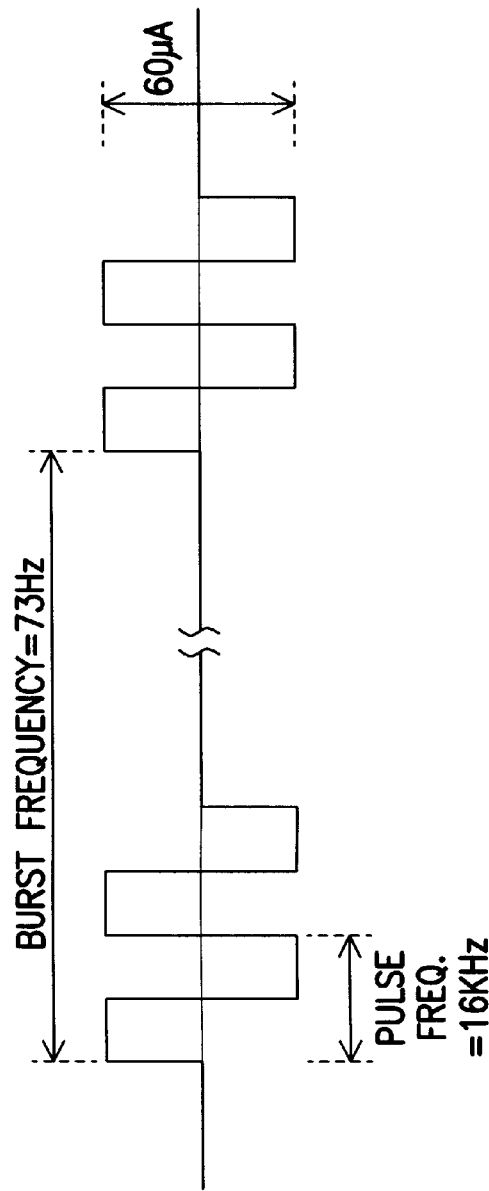
FIG. 5B is a trace of a current pulse used for measuring right ventricular function, according to one embodiment of the present system.

FIG. 5A shows a frequency chart according to one application and one embodiment demonstrating how the right ventricular frequency range of interest, 0.1 Hz to 25 Hz, is processed with a burst frequency of 73 Hz, which exceeds the calculated 50 Hz Nyquist frequency. The trace of FIG. 5B is one of many such current pulse waveforms which may be used to provide the required information for monitoring of the right ventricle. Other current pulse waveforms may be used without departing from the present system.

One way to conserve energy is to switch the 16 Khz pulse generator off when a burst is not being transmitted. The analog impedance signal processing circuits can also be switched off when not in use; they can be switched in synchrony with the burst of pulses to conserve energy.

The present signal processing system may be incorporated or used in combination with a variety of devices and applications, including, but not limited to, the devices and applications described in detail by the documents incorporated by reference in this patent application. Other devices and applications incorporating the present teachings will be readily apparent to those skilled in the art upon reading and understanding the present detailed description.

What is claimed is:

1. A method for producing an output related to a time-varying impedance of a load, comprising:

injecting current pulses of constant amplitude across the load using at least a first electrode and a second electrode, the current pulses including bursts of a plurality of pulses at a pulse frequency at which the current pulses are repeated, the bursts transmitted at a burst frequency;

detecting voltages across at least a third electrode and a fourth electrode;

high pass filtering the voltages to produce filtered voltages;

amplifying the filtered voltages to produce amplified voltage signals;

bandpass filtering the amplified voltage signals with a bandpass filter with a center frequency equal to approximately the pulse frequency to generate first filtered signals;

rectifying the first filtered signals to produce rectified signals;

integrating the rectified signals to produce integrated signals;

sampling-and-holding the integrated signals after each burst to capture an integrated pulse value for each burst, creating a plurality of discrete integrated pulse values; and bandpass filtering the plurality of discrete integrated pulse values using a filter including an upper cutoff frequency less than the burst frequency to produce the output related to the time-varying impedance of the load.

2. The method of claim 1, wherein the first electrode is positioned near to an apex of a right ventricle, the second electrode is outside of the right ventricle, the third electrode and fourth electrode are located within the right ventricle and wherein the output is related to the time-varying impedance of the right ventricle during systole and diastole.

3. The method of claim 2, comprising estimating stroke volume using the output.

4. The method of claim 2, comprising estimating hemodynamic maximum sensor rate using the output.

5. The method of claim 2, comprising controlling pacing as a function of the output.

6. The method of claim 2, wherein the second electrode comprises a housing of an implantable device.

7. The method of claim 2, wherein the burst frequency, the pulse frequency, and amplitude of the pulses are selected to provide low power consumption.

8. The method of claim 2, wherein the burst frequency exceeds about twice an expected maximum frequency of ventricular contraction and the pulse frequency is at least the burst frequency.

9. The method of claim 8, wherein the burst frequency is approximately 73 hertz and the pulse frequency is approximately 16 kilohertz.

10. The method of claim 9, wherein the pulses have a peak-to-peak amplitude of approximately 60 microamps and are biphasic.

11. The method of claim 9, wherein bandpass filtering the plurality of discrete integrated pulse values is performed using a switched capacitor bandpass filter having an upper cutoff frequency of about 30 hertz.

12. The method of claim 1, comprising analog-to-digital converting the output signal.

13. An apparatus, comprising:

an excitation source coupled to at least a first electrode and a second electrode, the excitation source producing current pulses of constant current flowing between the first electrode and the second electrode, the pulses sent in bursts at a burst frequency and having a pulse frequency at which the pulses are repeated;

a first high pass filter filtering voltage signals received by at least a third electrode and a fourth electrode to produce filtered voltage signals;

an amplifier amplifying the filtered voltage signals;

a first bandpass filter coupled to the amplifier and having a center frequency of approximately the pulse frequency;

a rectifier coupled to the first bandpass filter and rectifying the filtered and amplified voltage signals to produce rectified signals;

an integrator coupled to the rectifier and integrating the rectified signals to produce integrated signals;

a sample-and-hold coupled to the integrator and sampling-and-holding the integrated signals to produce a plurality of samples; and a second bandpass filter coupled to the integrator and including an upper band cutoff frequency which is less than the burst frequency, the second bandpass filter filtering the plurality of samples to produce an output signal related to a time-varying impedance of a load.

14. The apparatus of claim 13, wherein the first electrode is positioned near to an apex of a right ventricle, the second electrode is outside of the right ventricle, the third electrode and fourth electrode are adapted to be located within the right ventricle and wherein the output is related to the time-varying impedance of the right ventricle during systole and diastole.

15. The apparatus of claim 13, comprising an analog-to-digital convertor digitizing the output signal.

16. The apparatus of claim 13, further comprising means for estimating a stroke volume using the output.

17. The apparatus of claim 13, further comprising means for estimating a hemodynamic maximum sensing rate using the output.

18. The apparatus of claim 13, further comprising means for controlling pacing as a function of the output.

19. The apparatus of claim 13, wherein the second electrode comprises a housing of an implantable device.

20. The apparatus of claim 13, wherein the burst frequency, the pulse frequency, and amplitude of the pulses are selected to provide low power consumption.

21. The apparatus of claim 13, where the excitation source, amplifier, first bandpass filter, rectifier, integrator, sample-and-hold, and second bandpass filter are housed in a hermetically sealed housing implantable in a body.

22. The apparatus of claim 21, wherein at least a portion of the housing is electrically conductive and provides the first electrode or the second electrode.

23. The apparatus of claim 13, wherein the burst frequency exceeds about twice an expected maximum frequency of ventricular contraction and the pulse frequency is at least the burst frequency.

24. The apparatus of claim 23, wherein the burst frequency is approximately 73 hertz and the pulse frequency is approximately 16 kilohertz.

25. The apparatus of claim 23, wherein the pulses have a peak-to-peak amplitude of approximately 60 microamps and are biphasic.

26. The apparatus of claim 23, wherein the second bandpass filter comprises a switched capacitor bandpass filter having an upper cutoff frequency of about 30 hertz.

27. The apparatus of claim 23, wherein the first bandpass filter has a Q of 3.

* * * * *